United States Patent
Xia et al.

(10) Patent No.: US 10,378,041 B2
(45) Date of Patent: *Aug. 13, 2019

(54) EFFERVESCENT COMPOSITIONS AND USES THEREOF

(71) Applicant: 3M INNOVATIVE PROPERTIES COMPANY, St. Paul, MN (US)

(72) Inventors: Wensheng Xia, Woodbury, MN (US); Patrick A. Mach, Shorewood, MN (US); Joseph M. Beaurline, North St. Paul, MN (US); Jason W. Bjork, Cottage Grove, MN (US); Jie J. Liu, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,696

(22) Filed: Jan. 21, 2016

(65) Prior Publication Data

US 2016/0138070 A1    May 19, 2016

Related U.S. Application Data

(63) Continuation of application No. 13/989,922, filed as application No. PCT/US2011/066820 on Dec. 22, 2011, now Pat. No. 9,243,279.

(60) Provisional application No. 61/428,856, filed on Dec. 31, 2010.

(51) Int. Cl.
| | |
|---|---|
| C12Q 1/04 | (2006.01) |
| C12Q 1/689 | (2018.01) |
| C12N 1/14 | (2006.01) |
| C12N 1/38 | (2006.01) |
| C12N 1/20 | (2006.01) |

(52) U.S. Cl.
CPC .............. *C12Q 1/045* (2013.01); *C12N 1/14* (2013.01); *C12N 1/20* (2013.01); *C12N 1/38* (2013.01); *C12Q 1/04* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 2,985,562 A | * | 5/1961 | Millard ................ A61K 9/0007 424/44 |
| 3,622,677 A | | 11/1971 | Short et al. |
| 4,769,244 A | | 9/1988 | Lavie |
| 5,843,699 A | | 12/1998 | Strenkoski et al. |
| 6,432,450 B1 | | 8/2002 | Gergely et al. |
| 6,730,321 B2 | | 5/2004 | Ting et al. |
| 2001/0026792 A1 | | 10/2001 | Farrell et al. |
| 2003/0070691 A1 | | 4/2003 | Giletto et al. |
| 2008/0182272 A1 | | 7/2008 | Nagar et al. |

FOREIGN PATENT DOCUMENTS

| | | | |
|---|---|---|---|
| EP | 2 130 906 | 12/2009 | |
| FR | 2 559 499 | 8/1985 | |
| FR | 2559499 A1 | * 8/1985 | ........... C12N 5/0018 |
| GB | 1 270 781 | 4/1972 | |
| WO | WO 2009/147200 | 12/2009 | |
| WO | WO 2011/082309 | 7/2011 | |
| WO | WO 2011/119739 | 9/2011 | |
| WO | WO 2012/039901 | 3/2012 | |

OTHER PUBLICATIONS

Eng. MT. Demiaux, J.-B. et al. Aug. 16, 1985. New culture medium that is solid, fast, ready-to-use, and method for preparing same. European Patent Application Publication No. FR2559499 (A1). pp. 1-18. specif. pp. 3, 5, 6.*
Cole, E.T. et al.; "Enteric coated HPMC capsules designed to achieve intestinal targeting"; International Journal of Pharmaceutics; vol. 231; 2002; pp. 83-95.
Conte, U. et al.; "Press-coated tablets for time-programmed release of drugs"; Biomaterials; vol. 14, No. 13; 1993; pp. 1017-1023.
Jasson, V. et al.; "Kinetics of resuscitation and growth of *L. monocytogenes* as a tool to select appropriate enrichment conditions as a prior step to rapid detection methods"; Food Microbiology; vol. 26; 2009; pp. 88-93.
Lanz, W.W. et al.; "Timed-Release Capsule Method for Coliform Enumeration"; Applied and Environmental Microbiology; vol. 32, No. 5; 1976; pp. 716-722.
Lopes, C.M. et al.; "Compressed Matrix Core Tablet as a Quick/Slow Dual-Component Delivery System Containing Ibuprofen"; AAPS PharmSciTech; vol. 8, No. 3; Article 76; 2007; pp. E1-E8.
Sveum, W.H. et al.; "Timed-Release Capsule Method for the Detection of Salmonellae in Foods and Feeds"; Applied and Environmental Microbiology; vol. 33, No. 3; 1977; pp. 630-634.

* cited by examiner

*Primary Examiner* — Renee Claytor
*Assistant Examiner* — Sharon M. Papciak
(74) *Attorney, Agent, or Firm* — Eric E. Silverman (57) ABSTRACT

A latent effervescent body comprising a selective agent is disclosed. A method of using the latent effervescent body in a method to selectively enrich a target microorganism is also disclosed. The method comprises providing a sample, a culture medium, and the latent effervescent body. The method further comprises contacting the sample, the culture medium, and the latent effervescent body under conditions to facilitate growth of the target microorganism. The method further comprises releasing the selective agent from the latent effervescent body. Optionally, the method includes detecting a microorganism.

4 Claims, 2 Drawing Sheets

FIG. 1

FIG. 2

EFFERVESCENT COMPOSITIONS AND USES THEREOF

CROSS REFERENCE TO RELATED APPLICATIONS

This application is a continuation of U.S. patent application Ser. No. 13/989,922, filed May 28, 2013, which is a national stage filing under 35 U.S.C. 371 of PCT/US2011/066820, filed Dec. 22, 2011, which claims the benefit of U.S. Provisional Patent Application No. 61/428,856, filed Dec. 31, 2010, which is incorporated herein by reference in its entirety.

BACKGROUND

Rapid methods for the detection of pathogens in a sample (e.g., food) have been limited by the need for at least one enrichment step, which facilitates bacterial growth to a detectable level (e.g., to about $10^6$ colony forming units (cfu)/mL for ELISA detection methods). Current regulatory guidelines specify that a single cfu must be detected in a 25 gram sample of food. Available technologies cannot instantaneously detect a single bacterium in such a large sample. As a result, enrichment procedures are typically used to increase the number of microorganisms in the sample to facilitate detection.

Pathogens are typically injured during processing of products. That is, the pathogens may have undergone heating, freezing, contact with chemical additives, or mechanical processing steps which injure or debilitate the pathogens. Thus, resuscitation of the pathogens before detection is often required.

Because stressed microorganisms may be inhibited by selective agents that do not typically inhibit healthy microorganisms, a common technique for screening for the presence of pathogens involves the use of a series of media (i.e., nutrient fluid) transfers starting from the use of a non-selective enrichment medium, and then the use of a selective medium. The non-selective enrichment medium is usually employed to resuscitate potentially injured pathogens. Once the pathogens have been revived, a small quantity of the non-selective enrichment medium is then transferred into the selective medium. This technique, which is often defined by human work patterns and the growth patterns of the pathogens, generally takes several days to complete. Over the years, many attempts have been made to shorten the length of the primary enrichment step to reduce total assay time. Generally, it has been found that at least 8 to 24 hours of non-selective enrichment is required to obtain sufficient viable pathogens for further testing.

Detection methods involving pre-enrichment and selective enrichment steps are laborious and, because of their complexity, can be subject to a variety of human errors that may affect the result. A need exists for simpler enrichment procedures to obtain larger quantities of target microorganisms, or detectable biomolecule components thereof, in a sample.

SUMMARY

The present disclosure generally relates to the detection of a target microorganism in a sample that contains or may contain nontarget microorganisms. The inventive method provides a way to form a mixture of components including a sample, an aqueous growth medium, and an effervescent composition comprising a selective agent and an effervescent compound such that the selective agent is released into the growth medium at a predetermined time after the effervescent composition is contacted with the medium. Advantageously, the method permits the operator to expose the sample to a selective agent at a predetermined time after a liquid mixture is formed without having to separately add the selective agent to the mixture at the predetermined time. The method further provides a means for the selective agent to be mixed into the medium as it is released from the effervescent composition, thereby obviating the need to provide additional mixing force to distribute the selective agent throughout the liquid.

In one aspect, the present disclosure provides a method of enriching the growth of a target microorganism. The method can comprise providing a culture medium, a sample, and a latent effervescent body. The latent effervescent body can comprise an outer shell with a core composition disposed therein. The core composition can comprise two or more effervescent components and a selective agent that facilitates growth of the target microorganism relative to growth of at least one other microorganism. The method further can comprise contacting the sample, the latent effervescent body, and the culture medium under conditions to facilitate growth of the target microorganism. The method further can comprise releasing the selective agent from the latent effervescent body.

In any of the embodiments, releasing the selective agent further can comprise distributing the selective agent in the culture medium. In any of the above embodiments, distributing the selective agent further can comprise distributing the selective agent via a mixing process resulting from gaseous effervescence. In any of the above embodiments, releasing the selective agent further can comprise releasing the selective agent after an aqueous mixture comprising the sample and the culture medium are placed in fluidic contact with the latent effervescent body for a predetermined period of time. In any of the above embodiments, contacting the sample, the latent effervescent body, and the culture medium further can comprise contacting the sample with an effective amount of released selective agent for a period of time sufficient to permit selective enrichment of the target microorganism. In any of the above embodiments, the method further can comprise detecting a microorganism. In any of the above embodiments, detecting a microorganism can comprise propagating the microorganism on or in a semi-solid culture medium, observing the microorganism microscopically, detecting metabolic activity of the microorganism, detecting a biomolecule of the microorganism, or detecting a nucleic acid of the microorganism.

In another aspect, the present disclosure provides a latent effervescent body. The latent effervescent body can comprise an outer shell that disintegrates when contacted with an aqueous liquid and a core composition disposed therein. The core composition can comprise first and second effervescent components and a selective agent that facilitates growth of a target microorganism relative to growth of at least one other microorganism. In any of the embodiments, the latent effervescent body further can comprise a flow agent, a buffer component, a microbial growth indicator, a nutrient a binder, a disintegration aid, a lubricant, a filler, an anti-adhesion agent, or a combination of any two or more of the foregoing. In any of the above embodiments of the latent effervescent body, the outer shell can comprise polyvinyl alcohol, poly (meth)acrylate, cellulose and methylcellulose, derivatives of any of the foregoing, or mixtures of any of the foregoing. In any of the above embodiments of the latent effervescent body, the core composition can comprise a shaped composition. In any of the above embodiments of the latent effervescent body, wherein the outer shell can comprise a pouch. In any of the above embodiments of the latent effervescent body, the first effervescent component can comprise a base and the second effervescent component can comprise an acid. In any of the above embodiments of the latent effervescent body, the selective agent can comprise a salt, an antibiotic, a surfactant, or a bacteriocin. In any of the above embodiments of the latent effervescent body, the outer shell can be configured to release the core composition into the aqueous liquid after a predetermined amount of time. In any of the above embodiments of the latent effervescent body, the outer shell can comprise a mixture of ethylcellulose and hydroxypropyl methylcellulose. In some embodiments, the mixture of ethylcellulose and hydroxypropyl methylcellulose can comprise at least about 25 weight percent hydroxypropyl methylcellulose. In some embodiments, the mixture of ethylcellulose and hydroxypropyl methylcellulose can comprise at least about 33 weight percent hydroxypropyl methylcellulose. In some embodiments, the mixture of ethylcellulose and hydroxypropyl methylcellulose can comprise at least about 50 weight percent hydroxypropyl methylcellulose.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

"Selective agent", as used herein, refers to a chemical or biological compound or molecule that, when in fluidic contact with a susceptible microorganism, retards or prevents growth of the susceptible microorganism relative to its growth under similar conditions in the absence of the selective agent. It is recognized that susceptibility is a relative condition and that a microorganism (e.g., a target microorganism), while being somewhat susceptible to the selective agent, may be less susceptible to the selective agent than another microorganism (e.g., a non-target microorganism).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the description below. Other features, objects and advantages will become apparent from the description and from the claims.

DETAILED DESCRIPTION

The present disclosure relates to the detection of a target microorganism in a sample. In particular, the disclosure relates to the detection of a target microorganism in a sample that may comprise non-target microorganisms that, in some situations, may be present in the sample in significantly larger numbers than the target microorganism. Additionally, the disclosure relates to the detection of stressed microorganisms that may be present in a sample comprising non-target microorganisms.

The present disclosure recognizes that one problem with traditional methods of selective enrichment to detect pathogenic microorganisms is that, in order to detect stressed or injured microorganisms, two types of culture media must be used, a nonselective nutrient medium (to permit the resuscitation of injured target microorganisms) and a selective nutrient medium (to kill or inhibit the growth of non-target microorganisms). Additionally, this approach typically requires human intervention at a prescribed time to 1) add one or more extraneous selective agents to the batch enrichment (e.g., mixture of food sample, enrichment broth and microorganisms) or 2) transfer an aliquot of the batch enrichment, which includes a portion of the microorganisms, from the nonselective medium to the selective medium for further incubation. In either case, the final enrichment culture requires mechanical mixing to effectively distribute the sample and to assure an adequate representation of the enriched food sample.

The present disclosure provides a latent effervescent body for use in a method of enriching a target microorganism. The latent effervescent body is used in an inventive method that permits the operator to use a single nutrient medium to accomplish both the resuscitation step and the selective step, thereby obviating the need for the time-sensitive and labor-intensive intervention mentioned above. The inventive latent effervescent body permits the operator to add highly selective agents to a nonselective nutrient medium, wherein the selective agents do not exert their effects on microorganisms present in the medium for a predefined period of time. The inventive latent effervescent body further provides a means to instantaneously mix the ingredients of the selective agents into the nutrient medium without human or external mechanical intervention. The latent effervescent body and methods can be used in a method to detect the target microorganism.

The present disclosure provides a latent effervescent body. Latent effervescent bodies, according to the present disclosure, comprise an outer shell and a core composition disposed therein. A core composition, according to the present disclosure, comprises a selective agent that facilitates growth of a predetermined target microorganism, relative to at least one other microorganism, and at least two effervescent components.

Selective agents used in the core composition can be any selective agent known in the art to be useful to selectively enrich a target microorganism, provided the selective agent does not substantially interfere with the function of the outer shell of the latent effervescent body (e.g., either substantially accelerate or substantially inhibit the disintegration of the outer shell). Interference with the outer shell can easily be detected, for example, by monitoring (e.g., visually observing) and/or measuring (e.g., measuring the release of the colored reagent by spectroscopy, as described in Example 4) the disintegration of latent effervescent bodies made with and without the selective agent. Preferably, the selective agents do not substantially interfere with the stability and/or function of the effervescent components. Interference with the effervescent components can be monitored, for example, by monitoring (e.g., visually monitoring) the effervescence released by latent effervescent bodies made with and without the selective agent. Non-limiting examples of classes of selective agents include antibiotics (e.g., acriflavin), biocides, salts (e.g., LiCl), surfactants (e.g., bile salts), dyes, bacteriocins, and bacteriophage. Selective agents (e.g., acriflavin, LiCl) can be compounded in the latent effervescent bodies in amounts that can be used to deliver an effective concentration (e.g., 0.6 μg/mL acriflavin, 3 mg/mL LiCl) of the selective agent into the enrichment culture, as shown in the accompanying examples. Examples of other suitable selective agents include, but are not limited to, novobiocin, penicillin, acriflavin, nalidixic acid, cycloheximide, amphotericin B, streptomycin, ceftazidime hydrate, ampicillin, colistin, nisin, tetracycline, phenylethyl alcohol, desoxycholate, bile salts, oxgall, sodium thiosulfate, NaCl, methylene blue, brilliant green dye, crystal violet, and Malachite green.

Effervescent components used in the core composition include at least two components that, when combined in an aqueous solution, react to form a gaseous product (e.g., carbon dioxide). Preferably, the effervescent components used in the core composition are dry reagents (e.g., granules or powders, containing no more than about ambient moisture). At least one of the effervescent components in the core composition comprises an acid and at least one of the effervescent components in the core composition comprises a base. Non-limiting examples of suitable acid effervescent components include citric acid, tartaric acid, itaconic acid, and any other organic acid that reacts with the base effervescent component and does not substantially inhibit growth of the target microorganism. Non-limiting examples of suitable base effervescent components include sodium carbonate, sodium bicarbonate, potassium carbonate, potassium bicarbonate, lithium carbonate, lithium bicarbonate, and any other metal carbonate or metal bicarbonate compound that reacts with the acid effervescent component and does not substantially inhibit growth of the target microorganism. Preferably, the effervescent components do not substantially interfere with the stability and/or the function of the selective agent.

In addition to the selective agent and the effervescent components, the core composition optionally can further comprise other reagents such as, for example, a flow agent, a buffer component, a microbial growth indicator, a nutrient, a binder, a disintegration aid, a lubricant, a filler, an anti-adhesion agent, or a combination of any two or more of the foregoing.

Flow agents can be added to the core composition to assist in mixing the components of the core composition and in dispensing the mixture into a tablet mold, for example. Non-limiting examples of suitable flow agents include L-leucine and hydrophilic (e.g., fused) and/or hydrophobic silica particles (including nanoparticles, e.g. nanoparticles modified with isooctyltrimethoxysilane and methyltrimethoxysilane as disclosed in Example 1 of PCT Publication No. WO2012/039910, which is incorporated herein by reference in its entirety). Buffer components include buffering agents that can maintain the culture medium at an optimal pH to support the growth of the target microorganism. Non-limiting examples of suitable buffer components include sodium carbonate, disodium phosphate, sodium hydrogen phosphate, dipotassium phosphate, potassium hydrogen phosphate, MOPS, Tris, and HEPES. Microbial growth indicators include, for example, a pH indicator (e.g., neutral red, chlorophenol red, bromocresol purple) or an enzyme substrate (e.g., a chromogenic enzyme substrate such as orthonitrophenyl-α-D-glucopyranoside or paranitrophenyl-β-D-galactopyranoside, for example). Lubricants can be added to the core composition to reduce friction during tablet formation and to reduce friction during the ejection of the composition from a tablet-forming die cavity. Lubricants can be water-soluble or water-insoluble. Non-limiting examples of suitable water-soluble lubricants include boric acid, sodium oleate, and sodium acetate. Non-limiting examples of suitable water-insoluble lubricants include talc, magnesium stearate, calcium stearate, sodium stearate, wax, and sodium stearyl fumarate. Fillers can be added to the core composition, for example, to provide bulk that will aid in the handling of mixtures that comprise the core composition. Non-limiting examples of suitable fillers include lactose, sorbitol, mannitol, cellulose, and sucrose. Binders can be added to promote the cohesion of the components of the core composition during and after processing (e.g., during and after the process of forming shaped compositions such as tablets). Non-limiting examples of suitable binders include Polyvinyl Pyrrolidone, Polyethylene Glycol (PEG) 6000, Hydroxypropyl Methyl Cellulose (HPMC), and Hydroxypropyl Cellulose (HPC).

A disintegrant aid can facilitate the rapid disintegration of the latent effervescent body. Advantageously, this can permit rapid distribution of the selective agent throughout the culture medium by facilitating the penetration of the aqueous culture medium through a partially-disintegrated outer shell. Without being bound by theory, it is thought that, upon initial breach of the outer shell by the aqueous culture medium, the liquid contacts the disintegration aid, causing the disintegration aid to absorb the liquid and to swell. The swelling of the disintegration aid puts additional pressure (i.e., in addition to the pressure from the gaseous effervescence) on the weakened outer shell, causing it to split more quickly than it would in the absence of such additional pressure. Non-limiting examples of suitable disintegration aids include water-swellable polymers such as carboxymethylcellulose (e.g., AC-DI-SOL Croscarmellose sodium, available from FMC Biopolymer, Philadelphia, Pa.), cross-linked polyvinylpyrrolidone (e.g., POLYPLASDONE XL-10, available from International Specialty Products, Wayne, N.J.), and sodium starch glycolate (e.g., PRIMOJEL sodium starch glycolate, available from DMV-Fonterra Excipients, Princeton, N.J.), for example.

In some embodiments, the components of the core composition can be used to make a shaped composition (e.g., a tablet). Processes for making compositions having generally uniform sizes and shapes are known in the art and include, for example, using a tableting punch die (e.g., a single-head punch die). The punch die can be used with a mechanical press, in order to obtain uniform compaction of each tablet. In some embodiments, the components of the core composition can be milled prior to forming the shaped composition, in order to obtain a homogeneous mixture of the components.

The outer shell of the latent effervescent body is configured to release the core composition into an aqueous liquid (e.g., water, an aqueous buffer, a culture medium) after a predetermined amount of time. That is, the outer shell comprises a material (e.g., a polymeric material) that is partially, but not completely, resistant to the penetration of an aqueous liquid therethrough. However, after a period of time, the aqueous liquid can completely penetrate the outer shell and react with the core composition.

In some embodiments, the water resistance of the outer shell can be controlled by fabricating the outer shell from a material with a predetermined susceptibility to penetration and/or disintegration by water. Polyvinylalcohol ("PVA"), for example, is available, for example from Kuraray America (Houston, Tex.), in several grades that have relatively slow or relatively fast dissolution rates in water (e.g., Kuraray grades 28-99 and 30-92, respectively). In these embodiments, the polymer can be dissolved in water, cast onto a carrier (e.g., a plastic film), dried, and the dried PVA film can be removed from the carrier. The dried film can be used to make a latent effervescent body by depositing the components of the core composition (which may be in the form of a shaped composition) onto the central portion of a first PVA film, overlaying the first PVA film (having the core composition thereon) with a second PVA film, and sealing (e.g., adhesively sealing or heat-sealing) the films together to form a pouch containing the core composition. Care can be taken during the heat-sealing process to eliminate as much air as possible from the pouch, thereby providing optimal contact between the core composition and the PVA outer shell. It is contemplated that dried films used to form a pouch configuration of the latent effervescent body can be formed from a blend comprising two or more distinct polymers. Polymer films that can be used to form a pouch configuration of a latent effervescent body can also be purchased. Examples of such films include, for example, SOLUBLON grades EF-30, BP-26, and KA-40, all available from Aicello Chemical Co. (Aichi, JP).

Figure 2:
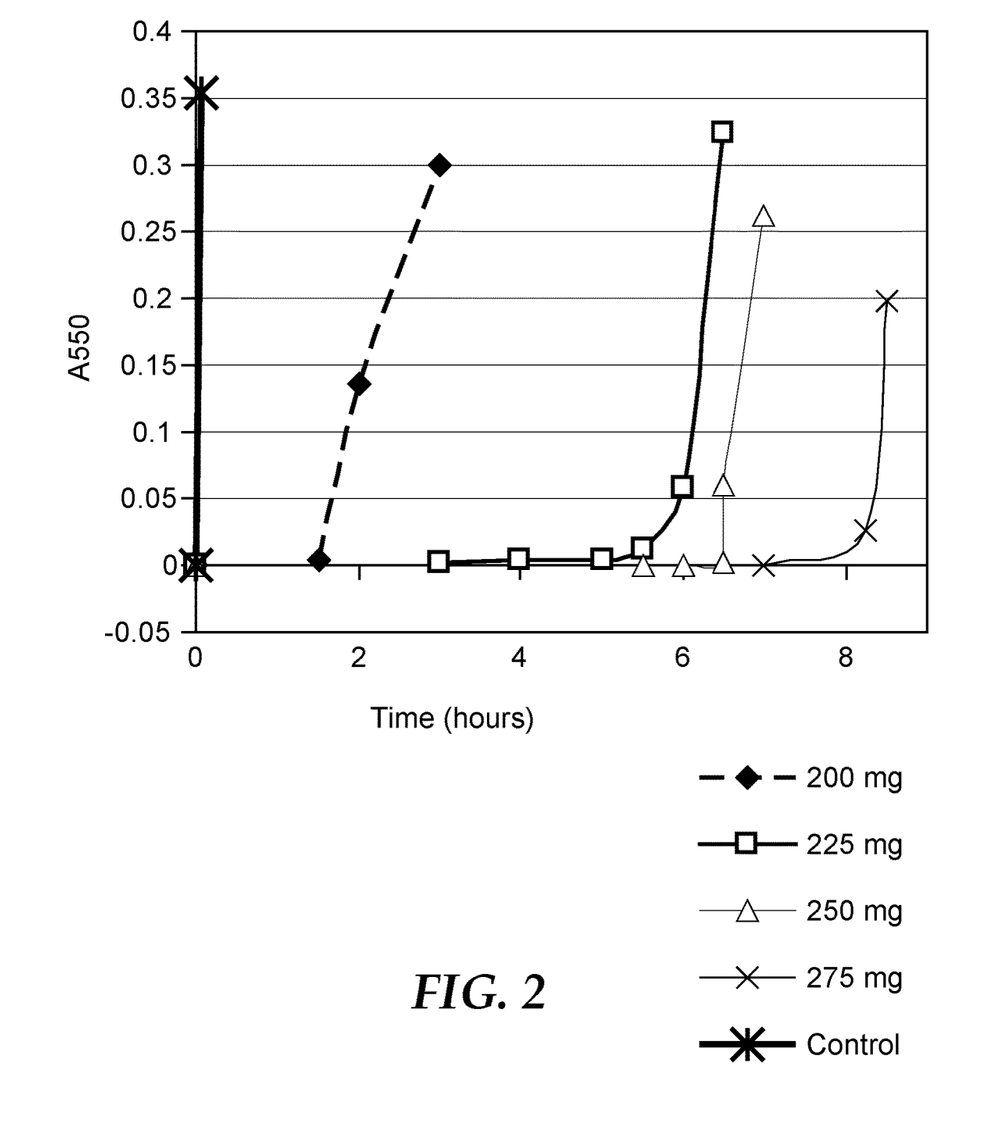
FIG. 2 is a graph the absorbance of visible light, over a period of time, in individual aqueous solutions to which different embodiments of effervescent compositions of the present disclosure have been added.

In some embodiments, the water-resistance of the outer shell can be controlled by fabricating the outer shell from a mixture of two or more materials, a first material being substantially water-resistant and a second material being relatively less water resistant. By adjusting the ratios of the two or more materials in the outer shell and/or by adjusting the thickness of the outer shell, the operator can fabricate a latent effervescent body that is configured to release the core composition into an aqueous liquid. In general, the more first material you have in the mixture, the longer it takes for an aqueous solution to penetrate the outer shell. In some embodiments, the first and second materials are polymeric materials. In any embodiment, the first material can be ethylcellulose, hereinafter "ETC" (e.g., 10 cp, 48% ethoxylated ethylcellulose; available from Sigma-Aldrich; St. Louis Mo.) or Eudragit RS/RO (a polyacrylate polymer available from Evonik Degussa International; Newark, Del.), for example. In any embodiment, the second material can be hydroxypropylcellulose, hereinafter "HPC" (e.g., fine grind Klucel EXF hydroxypropylcellulose; available from Hercules Inc.; Willmington Del.), hydroxypropylmethylcellulose (available from Dow Chemical Company, Newark, Del.), or an anionic copolymer of methacrylic acid and methyl methacrylate (e.g., EUDRAGIT L-100, available from Evonik Degussa International; Newark, Del.), for example. The first and second materials (e.g., ETC and HPC, respectively) can be combined in a mixture comprising less than or equal to about 75 weight percent ETC, less than or equal to about 67 weight percent ETC, less than or equal to about 50 weight percent ETC. The effects of various ratios of first and second materials on the disintegration of latent effervescent bodies and a simple method to measure the disintegration rate are shown in FIG. 2 and described in Example 4 below. Mixtures of two or more outer shell materials can be dissolved, cast into films, and used to make a pouch configuration of a latent effervescent body, as described above. Additionally, mixtures of two or more polymers can be used in the alternative outer shell-forming processes described below.

Alternatively, the outer shell can be formed around the core composition using a process similar to the process used to form the shaped core composition. In this alternative process, the components of the core composition are used to form a shaped composition using a first tableting punch die, for example, as described above. A first portion (e.g., about 50%) of the outer shell material(s) is placed into a second, larger, punch die cavity. The shaped composition from the first punch die is placed (e.g., approximately in the center) of the second punch die cavity, on top of the outer shell material. The remainder of the outer shell material(s) is deposited on top of the shaped composition in the second punch die and the appropriate pressure (e.g., about 1360 kg) is applied to the punch die to for the latent effervescent body having a core composition and an outer shell.

Alternatively, the outer shell can be formed around the core composition using a coating process. In this alternative process, the components of the core composition are used to form a shaped composition using a first tableting punch die, for example, as described above. The shaped composition can then be coated with a liquid solution containing materials that form the outer shell (e.g., an anionic copolymer of methacrylic acid and methyl methacrylate, ethylcellulose, hydroxypropylcellulose, hydroxypropylmethylcellulose, polyvinyl alcohol, and the like or combinations thereof). The shaped compositions can be coated using any liquid coating process known in the art such as dip coating, curtain coating, or spray coating, for example. The composition of the coating, as well as the thickness of the coating will control the amount of time it takes an aqueous liquid to penetrate and/or disintegrate the outer shell and release the core composition. Thus, to delay the release of the core composition for longer periods, it is contemplated that several layers (e.g., 2 layers, 3 layers, 4 layers, 5 layers) of the coating may be applied. It is also contemplated that each layer of a multi-layer outer shell may comprise the same materials or they may comprise different materials, in order to control the release of the core composition.

Alternatively, In some embodiments, a latent effervescent body of the present disclosure can be produced by loading the core composition into a pre-formed capsule such as, for example, the type of capsule used to encapsulate medicaments. The pre-formed capsule can be formed from a cellulose-based material and may be provided in two oblong halves, with complementary openings at one end that allow the halves to be joined by friction-fit, as is customary for capsules loaded with powdered medicaments in the pharmaceutical industry. A core composition comprising powders of the effervescent components (e.g. sodium bicarbonate and citric acid), a selective agent (e.g., acriflavin HCl), and a flow agent (e.g. fused silica particles) can be loaded into one half of the capsule and the loaded half can be joined by friction-fit to the other half of the capsule. Optionally, the edges of the filled, assembled capsule can be sealed with a liquid solution (e.g., a solution of hydroxypropylmethylcellulose) solution like the Capsule Band-sealing equipment made from Qualicaps Group and a coating solution (e.g., a mixture of ethylcellulose and HPMC, or Eudragit S100 or L100 in ethanol or isopropanol) can be spray-coated onto the capsules, as described herein. The thickness of the coating can be measured by the weight gain, and a predetermined delay-time for the release of the core composition can be achieved.

Spray coating is a preferred liquid coating method for tablet. Typically, a batch at least 600 g of tablets (approximately 250 mg each) is put into a rotated coating pan. The coating solution, either in aqueous or organic solvent, is sprayed via a nozzle to generate atomized mist near the coating pan, which is held at an elevated temperature under venting system to dry the coated tablets. A dry coating weight equal to about 2-20% of the weight of the tablet provides a useful delayed-release time for the core composition of the coated tablet. An exemplary coating machine is the Hi-coater coating machine, available from Vector Corporation, Marion, Iowa.

Figure 1:
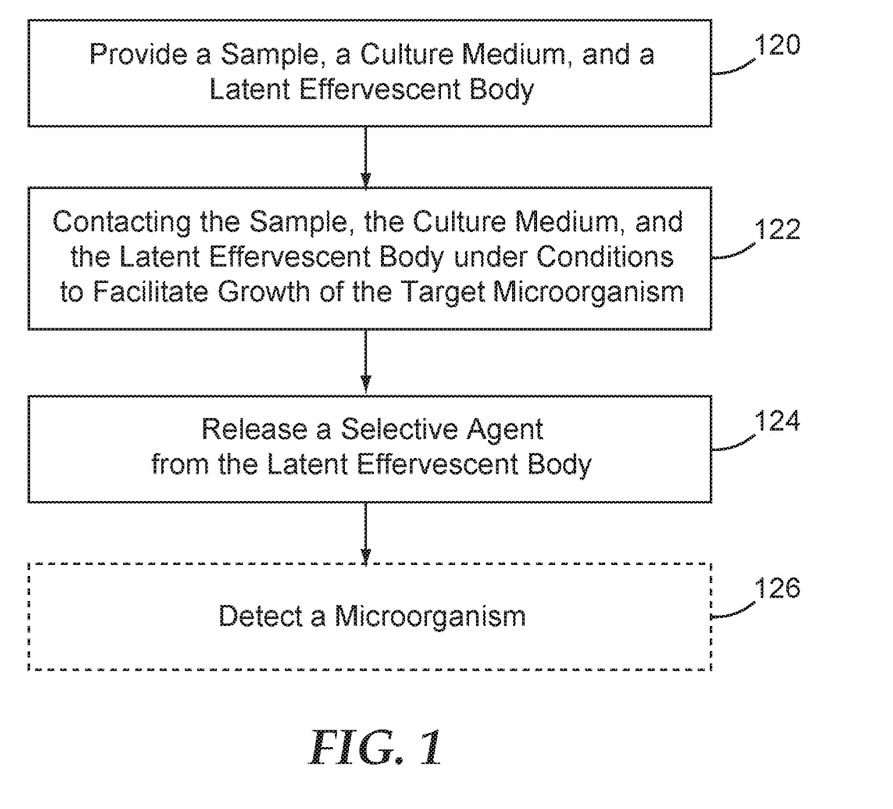
FIG. 1 is a block diagram of one embodiment of a method of enriching a microorganism according to the present disclosure.

The present disclosure provides a method of selectively enriching a target microorganism. It should be understood that the target microorganism is a predetermined microorganism (i.e., predetermined by the operator who is performing the method) and that many aspects of the method (e.g., the type, formula, and supplier of the culture medium or media, the selective agents, the incubation times and temperatures) are selected by the operator and/or prescribed by a reference method to facilitate the enrichment of the particular target microorganism from a given sample material. FIG. 1 shows a block diagram of one embodiment of a method of selectively enriching a microorganism according to the present disclosure. The method includes the step 120 of providing a sample, a culture medium, and a latent effervescent body.

"Selective enrichment", as used herein, refers to a process whereby a sample is subjected to conditions, including the addition of a selective agent to the sample, that facilitate growth of a predetermined target microorganism. These conditions include, but are not limited to, a nutrient environment with sufficient water activity to promote the growth of the target microorganism, a temperature that supports the growth of the target microorganism, and a selective agent that is chosen to enhance the growth of the target microorganism relative to at least one non-target microorganism.

The sample can be any sample that may contain a target microorganism to be selectively enriched. Nonlimiting examples of suitable samples include environmental samples (e.g., surface swabs/sponges, soil, sediments, fomites), food (e.g., raw materials, in-process samples, and finished-product samples), starter cultures, beverages, clinical/veterinary samples (e.g., blood, serum, plasma, urine, sputum, tissue, mucous, feces, wound exudate, pus, cerebrospinal fluid), and water (e.g., surface water, potable water, process water).

In some embodiments, the target microorganism can be enriched using a sample that is derived from a variety of food, beverage, or food- or beverage-processing environmental sources. Non-limiting examples of food sources include raw or processed meat, raw or processed fruits or vegetables, non-fluid dairy products (e.g., cheese, butter, and ice cream), starter cultures, nuts, spices, ingredients, and syrups. Non-limiting examples of beverage sources include potable water, fruit or vegetable juices, milk, and fermented beverages. Pasteurized food or beverages may also be suitable sources. Nonlimiting examples of food- or beverage-processing environmental samples include food-handling surface samples (e.g., conveyor belts, blades, cutting surfaces, mixing equipment surfaces, filters, storage containers), room samples (e.g., walls, floors, drains, ventilation equipment), and cleaning equipment (e.g., hoses, cleaning tools).

In some embodiments, the target microorganism can be enriched using a sample that is derived from a variety of human or animal sources, such as a physiological fluid, e.g., blood, saliva, ocular lens fluid, synovial fluid, cerebral spinal fluid, pus, sweat, exudate, urine, mucus, lactation milk, or the like. Further, the test sample may be derived from a body site, e.g., wound, skin, nares, scalp, nails, etc.

Samples of particular interest from human or animal sources include fecal samples, as well as mucous-containing samples and samples from mucosal tissue, the outer ear, middle ear, mouth, rectum, vagina, or other similar tissue. Examples of specific mucosal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Suitable samples for methods of the present disclosure can include certain solid samples. Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

Target microorganisms of particular interest include prokaryotic and eukaryotic organisms, particularly Gram positive bacteria, Gram negative bacteria, fungi, *Mycoplasma*, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V. parahemolyticus*, *Salmonella choleraesuis*, *cholcrasuis*, *S. typhi*, *S. typhimurium*, *Candida albicans*, *C. glabrata*, *C. krusei*, *Cronobacter sakazakii*, *E. coli* O157 and multiple drug resistant Gram negative rods (MDR).

Gram positive and Gram negative bacteria are of particular interest. Of particular interest are Gram positive bacteria, such as *Listeria monocytogenes*. Also, of particular interest are antibiotic resistant microbes including MRSA, VRSA, VISA, VRE, and MDR microbes.

In addition to providing a sample, the method comprises providing a culture medium. The culture medium is selected to facilitate growth of the target microorganism. "Growth" is used herein in its broadest sense and refers to anabolic cellular activities including, for example, protein synthesis, nucleic acid synthesis, cell membrane synthesis, cell wall synthesis, cell division or any combination of two or more of the foregoing cellular activities. Generally, the culture medium comprises water, essential minerals, and nutrients to support the growth of the target microorganism. The particular culture medium may be selected based upon the target microorganism to be enriched and the selection of the appropriate culture medium is well within the ambit of a person having ordinary skill in the art.

Referring back to FIG. 1, a method of the present disclosure further comprises the step 122 of contacting the sample, the latent effervescent body, and the culture medium under conditions to facilitate growth of the target microorganism. Typically, the culture medium is an aqueous liquid. In some embodiments, the culture medium is housed in a container, such as a flask, a beaker, a bag, a tube, a Petri dish, a multi-well plate, or the like. Preferably, the container is sterilized before the culture medium is placed therein or the container is sterilized with the culture medium in situ. The sample and the culture medium can be brought into contact by transferring the culture medium to a container holding a sample or by transferring the sample to a container holding the culture medium. In some embodiments, the sample and the culture medium can be brought into mutual contact in a first container (e.g., a blender jar, a sample bag or a stomacher bag) and, subsequently, all or a portion of the sample/culture medium mixture can be transferred to a second container (e.g., a tube or a flask) for incubation. A latent effervescent body can be brought into contact with the sample and the culture medium in a variety of ways. The latent effervescent body can be deposited into an empty container, to which the culture medium and sample can be added sequentially (in any order), simultaneously, or as a mixture. Alternatively, the latent effervescent body can be transferred to a container holding the sample, the culture medium, or the culture medium and the sample; with the other component (sample or culture medium), if not already present, added subsequently. In a preferred embodiment, the sample and the culture medium are brought into contact in a container and the latent effervescent body transferred to the container shortly thereafter. In some embodiments, the culture medium may be brought into contact with the sample and the resulting composite mixture can be incubated for a period of time before the latent effervescent body is contacted with the mixture.

Conditions facilitating the growth of the target microorganism are recognized by a person having ordinary skill in the art and may include, but are not limited to, the nutrient composition of the culture medium, the pH of the culture medium, the ionic strength of the culture medium, exposure of the culture medium to light, the oxygen tension of the culture medium, and the temperature of the culture medium during the incubation phase (e.g., in an incubator). It will be recognized that some of these conditions (e.g., pH, temperature) may also affect the amount of time it takes for the latent effervescent body to disintegrate. This can be determined by screening the outer shell materials (under similar conditions of pH and temperature) according to the simple procedure described in Example 4.

Methods of the present disclosure further comprise the step 124 of releasing the selective agent from the latent effervescent body. Preferably, the selective agent is released after an aqueous mixture comprising the sample and the culture medium are placed in fluidic contact with the latent effervescent body for a predetermined period of time. The contact between the latent effervescent body and an aqueous fluid initiates the process of disintegrating the outer shell, which ultimately results in the release of the core composition. Advantageously, by delaying the release of the selective agent for a predetermined period of time, any injured or stressed target microorganisms in the original sample will have time to substantially resuscitate and grow in the culture medium before the selective agent is released. In some embodiments, the predetermined time is less than or equal to about 24 hours after contact between the sample, culture medium, and the latent effervescent body. In some embodiments, the predetermined time is about 30 minutes or longer, but less than about 24 hours, after contact between the sample, culture medium, and the latent effervescent body. In some embodiments, the predetermined time is about 30 minutes or longer, but less than or equal to about 2 hours, after contact between the sample, culture medium, and the latent effervescent body. In some embodiments, the predetermined time is about 2 hours or longer, but less than or equal to about 6 hours, after contact between the sample, culture medium, and the latent effervescent body. In some embodiments, the predetermined time is less than about 2 hours after contact between the sample, culture medium, and the latent effervescent body. In some embodiments, the predetermined time is about 2 hours or longer, but less than or equal to about 12 hours, after contact between the sample, culture medium, and the latent effervescent body.

Typically, after the release of the selective agent from the latent effervescent composition, the mixture comprising the sample, the culture medium and the selective agent is contacted (e.g., incubated) for a period of time. This additional contact time permits an effective amount of the selective agent to be released from the latent effervescent body and, thereby, to inhibit or prevent the growth of at least one non-target microorganism. The additional contact time may also permit an increase in the number of target microorganisms, or biomolecules thereof (e.g., nucleic acid molecules, proteins, polysaccharides, lipids, enzymes, antigens), in the culture medium.

Methods of the present disclosure further comprise the optional step 126 of detecting a microorganism. In some embodiments, detecting a microorganism can comprise detecting a target microorganism. In some embodiments, detecting a microorganism can comprise detecting a non-target microorganism. The microorganism can be detected by any microorganism detection means known in the art including, but not limited to optical (e.g., microscopy, flow cytometry) detection, plating techniques (e.g., using agar culture media or dry, rehydratable film-based culture device and the like), immunoassay techniques (e.g., ELISA, agglutination, lateral-flow immunoassays), an enzyme assay, a molecular genetic technique (e.g., isothermal nucleic acid amplification methods, PCR, LCR, NASBA, PFGE), and bacteriophage typing.

EMBODIMENTS

Embodiment 1 is a method of method of enriching the growth of a target microorganism, comprising:
providing a culture medium, a sample that may include the target microorganism, and a latent effervescent body;

wherein the latent effervescent body comprises an outer shell with a core composition disposed therein
wherein the core composition comprises two or more effervescent components and a selective agent that facilitates the growth of the target microorganism relative to growth of at least one other microorganism;
contacting the sample, the latent effervescent body, and the culture medium under conditions to facilitate growth of the target microorganism; and
releasing the selective agent from the latent effervescent body.

Embodiment 2 is the method of embodiment 1, wherein releasing the selective agent further comprises distributing the selective agent in the culture medium.

Embodiment 3 is the method of embodiment 2, wherein distributing the selective agent further comprises distributing the selective agent via a mixing process resulting from gaseous effervescence.

Embodiment 4 is the method of any one of embodiments 1 through 3, wherein releasing the selective agent further comprises releasing the selective agent after an aqueous mixture comprising the sample and the culture medium are placed in fluidic contact with the latent effervescent body for a predetermined period of time.

Embodiment 5 is the method of any one of the preceding embodiments, wherein the predetermined time is less than or equal to 24 hours.

Embodiment 6 is the method of embodiment 5, wherein the predetermined time is about 30 minutes to about 24 hours.

Embodiment 7 is the method of embodiment 6, wherein the predetermined time is about 30 minutes to about 2 hours.

Embodiment 8 is the method of embodiment 6, wherein the predetermined time is about 2 to about 6 hours.

Embodiment 9 is the method of embodiment 5, wherein the predetermined time is less than 2 hours.

Embodiment 10 is the method of any one of the preceding embodiments, wherein contacting the sample, the latent effervescent body, and the culture medium further comprises contacting the sample with an effective amount of released selective agent for a period of time sufficient to permit selective enrichment of the target microorganism.

Embodiment 11 is the method of any one of the preceding embodiments, further comprising detecting a microorganism.

Embodiment 12 is the method of embodiment 11, wherein detecting the microorganism comprises propagating the microorganism on or in a semisolid culture medium, observing the microorganism microscopically, detecting metabolic activity of the microorganism, detecting a biomolecule of the microorganism, or detecting a nucleic acid of the microorganism.

Embodiment 13 is a latent effervescent body, comprising;
an outer shell that disintegrates when contacted with an aqueous liquid; and
a core composition disposed therein;
wherein the core composition comprises first and second effervescent components and a selective agent that facilitates growth of a target microorganism relative to growth of at least one other microorganism.

Embodiment 14 is the latent effervescent body of embodiment 12, further comprising a flow agent, a buffer component, a microbial growth indicator, a nutrient, a binder, a disintegration aid, a lubricant, a filler, an anti-adhesion agent, or a combination of any two or more of the foregoing.

Embodiment 15 is the latent effervescent body of embodiment 12, wherein the core composition comprises the disintegration aid.

Embodiment 16 is the latent effervescent body of any one of embodiments 12 through 14, wherein the outer shell comprises polyvinyl alcohol, poly(meth)acrylate, cellulose and methylcellulose, propylcellulose, derivatives of any of the foregoing, or mixtures of any of the foregoing.

Embodiment 17 is the latent effervescent body of any one of embodiments 12 through 15, wherein the core composition comprises a shaped composition.

Embodiment 18 is the latent effervescent body of any one of embodiments 12 through 16, wherein the outer shell comprises a pouch.

Embodiment 19 is the latent effervescent body of embodiment 17, wherein the outer shell conforms to the shape of the shaped composition.

Embodiment 20 is the latent effervescent body of any one of embodiments 12 through 18, wherein the first effervescent component comprises a base and the second effervescent component comprises an acid.

Embodiment 21 is the latent effervescent body of any one of embodiments 12 through 19, wherein the first effervescent component comprises sodium carbonate, sodium bicarbonate, potassium carbonate, potassium bicarbonate, lithium carbonate, lithium bicarbonate, or a mixture of any two or more of the foregoing.

Embodiment 22 is the latent effervescent body of any one of embodiments 12 through 20, wherein the second effervescent component comprises citric acid, tartaric acid, itaconic acid, or a mixture of any two or more of the foregoing.

Embodiment 23 is the latent effervescent body of any one of embodiments 13 through 22, wherein the microbial growth indicator comprises a pH indicator, an enzyme substrate, or a redox indicator.

Embodiment 24 is the latent effervescent body of any one of embodiments 12 through 23, wherein the selective agent comprises a salt, an antibiotic, a surfactant, a dye, or a bacteriocin.

Embodiment 25 is the latent effervescent body of embodiment 24, wherein the selective agent is selected from the group consisting of novobiocin, penicillin, acriflavin HCl, nalidixic acid, cycloheximide, amphotericin B, streptomycin, ceftazidime hydrate, ampicillin, colistin, nisin, tetracycline, phenylethyl alcohol, sodium desoxycholate, sodium dodecylsulfate, bile salts, oxgall, sodium thiosulfate, NaCl, lithium chloride, lithium carbonate, methylene blue, brilliant green dye, crystal violet, and Malachite green.

Embodiment 26 is the latent effervescent body of any one of embodiments 13 through 25, wherein the outer shell is configured to release the core composition into the aqueous liquid after a predetermined amount of time.

Embodiment 27 is the latent effervescent body of embodiment 26, wherein the outer shell comprises a mixture of ethylcellulose and hydroxypropyl methylcellulose or hydroxypropylcellulose.

Embodiment 28 is the latent effervescent body of embodiment 27, wherein the mixture of ethylcellulose and hydroxypropyl methylcellulose comprises at least about 25 weight percent hydroxypropyl methylcellulose.

Embodiment 29 is the latent effervescent body of embodiment 28, wherein the mixture of ethylcellulose and hydroxypropyl methylcellulose comprises at least about 33 weight percent hydroxypropyl methylcellulose.

Embodiment 30 is the latent effervescent body of embodiment 29, wherein the mixture of ethylcellulose and hydroxypropyl methylcellulose comprises at least about 50 weight percent hydroxypropyl methylcellulose.

EXAMPLES

Unless otherwise stated, all percentages and parts are by weight. As used herein, a disintegration aid may also be referred to as a disintegrant.

Materials Used

SIL1—CAB-O-SIL TS-530 surface modified fumed silica; Cabot Corporation; Boston Mass.

SIL2—AEROSIL 200 fumed silica; Evonik DeGussa Corporation; Parsippany N.J.

Silica Nanoparticles—nanoparticles modified with isooctyltrimethoxysilane and methyltrimethoxysilane as disclosed in Example 1 of co-pending patent application U.S. Patent Application No. 61/384,574.

Methacrylic acid-methyl methacrylate copolymer having ratio of carboxyl groups to ester groups of 1:1—Eudragit™ L100 polymer (Evonik Corporation; Piscataway N.J.)

Magnesium Stearate NF (EM Science; Gibbstown N.J.)

Lithium carbonate powder (J. T. Baker; Philipsburg N.J.)

Disintegration aid—Croscarmellose sodium type A (Ac-Di-Sol™ polymer; FMC BioPolymer; Philadelphia Pa.)

Leucine (Sigma-Aldrich; St. Louis Mo.)

ETC1—Ethylcellulose (10 cp, 48% ethoxyl; Sigma-Aldrich; St. Louis Mo.)

ETC2—Ethylcellulose (Ethocel P10; Dow Chemical Co.; Philadelphia Pa.)

HPC hydroxypropylcellulose, fine grind (Klucel EXF; Hercules Inc.; Wilmington, Del.)

HPMC—hydroxypropyl methylcellulose (Methocel E5; Dow Chemical Co.; Philadelphia Pa.)

Reagents obtained from Sigma Aldrich; St. Louis Mo.:
  Acriflavin HCl
  PBS Buffer—Phosphate buffer saline solution Reagents obtained from Spectrum Laboratories; Gardena Calif.:
  PVP—Polyvinylpyrrolidone (PVP K30)
  Sodium Stearyl fumarate NF
  Sodium carbonate powder
  Sodium bicarbonate powder
  Sorbitol
  Citric acid powder
  Lactose Bacterial stock culture of *Listeria monocytogenes* (ATCC 11994)—The American Type Culture Collection, Manassas, Va. A streak plate is prepared by streaking a SBA plate with the stock culture and incubating overnight at 35° C.

Tryptic Soy Agar plate—Difco™ Tryptic Soy Agar obtained from Becton Dickinson, Sparks, Md., prepared at 3 weight percent (wt %) according to the manufacturer's instructions using Difco™ Tryptic Soy Broth, Becton Dickinson, Sparks, Md.

Butterfield's Phosphate diluent (also referred to as Butterfield's Buffer)—3M Company; St. Paul Minn.

Tryptic soy broth—3M Company; St. Paul Minn.

Media obtained from Hardy Diagnostics; Santa Maria Calif.)
  MOX plate—Oxford Medium, Modified for *Listeria*, agar-based growth medium
  Blood agar plate—Tryptic soy agar with 5% sheep's blood;

Example 1. Production of Coated Tablets Containing a Disintegration Aid

A tablet composition was prepared by adding the materials listed in Table 1 for Example 1 to a 10 mL ball-mill tube. The total amount of the batch was 2.04 grams. The tube was equipped with a 1.25 cm diameter ball and the composition was processed on a mixer mill (Model MM300 mixer mill; Retsch Inc.; Newtown Pa.) for 60 seconds at a frequency of 16'. Approximately 20 mg of the milled composition was placed into each of six 3-mm diameter round cavities in a tabletting punch die. The mating die having a push rod corresponding to each cavity was positioned over the cavities and compressed with a hand press for form tablets. Each of the tablets weighed about 19 mg. Ten tablets, prepared in this manner were placed in 10 mL of DI water. All of the tablets completely dissolved in 10-20 minutes.

A coating solution was prepared by dissolving 7.5% Eudragit L100 polymer and 3.25% ETC1 in ethanol Tablets were dip-coated on one side, dried in hot air at 60° C., and then dipped and dried on the other side, taking care to coat the entire tablet. The process was repeated twice to provide 3 layers of coating on the tablet. Ten coated tablets, placed in about 20 mL of DI water dissolved completely in about 3 hours.

Example 2. Production of Effervescent Tablets

A tablet composition having the materials shown in Table 1 for Example 2 were prepared according to the procedure described in Example 1. The tablets weighed about 18 mg each, and contained about 4.5 mg acriflavin in each tablet. Gas bubbles were generated when 10 tablets were placed in 10 mL of DI water. The tablets dissolved in 1-2 minutes and a homogenous solution resulted after the gas bubbled off

TABLE 1

| Material | Tablet Composition - Weight % | |
|---|---|---|
|  | Example 1 | Example 2 |
| CAB-O-SIL TS-530 | 0.25 | 0.25 |
| Leucine | 5.00 | 5.00 |
| PVP | 5.00 | 5.00 |
| Disintegration aid | 1.00 |  |
| Lactose | 55.42 |  |
| Sorbitol |  | 55.00 |
| Sodium bicarbonate |  | 5.53 |
| Citric acid |  | 4.22 |
| Acriflavin HCl | 33.33 | 25.00 |

Example 3. Preparation of Tablets with Varying Coating Thicknesses

A core tablet composition was prepared by adding the amounts of materials listed for Example 3 in Table 2 to a 200 mL glass jar and vortexing for 2 minutes. The batch size was 20 grams. A tabletting punch die with a 0.3125 inch diameter was filled with 250 mg of the composition and compressed on a semi-automatic press (Carver Inc.; Wabash Ind.) with a force of 3,000 pounds to form a 250 mg tablet.

A second tabletting punch die with a 0.5 inch diameter was used to prepare coated tablets. Mixtures of ETC1 and HPMC powders in ratios of 1:2, 1:1, and 2:1 were stirred together. Core tablets were coated with each mixture and with ETC1 alone. For each tablet, 120 mg of the powder was placed in the die cavity and tamped flat. A core tablet was centered on the powder, and another 120 mg of the mixture was added to cover the tablet. The die was compressed with 3000 pounds force to form a coated tablet.

The procedure was repeated for each of the powders. A coated tablet was placed in 40 mL of PBS buffer and monitored for dissolution. Tablets with a 2:1 ratio dissolved for over 6 hours, and tablets with 1:2 and 1:1 ratios dissolved in about 3 hours.

TABLE 2

| | Tablet Composition-weight % | |
|---|---|---|
| Material | Example 3 | Example 4 |
| Silica Nanoparticle | 1.00 | 1.00 |
| Leucine | 5.00 | 5.00 |
| PVP | 10.00 | 10.00 |
| Sodium bicarbonate | 31.00 | 31.00 |
| Citric acid | 23.65 | 23.65 |
| Sorbitol | 29.25 | 24.25 |
| Phenol red | 0.10 | 0.10 |
| Disintegration aid | 0 | 5.00 |

Example 4. Preparation of Coated Tablets with Disintegration Aid

Core tablets were prepared using the materials in Table 2 for Example 4, and coated with a 2:1 ratio of ETC1 to HPMC powder mixture according to the procedure described in Example 3. The cavity was filled with 200 mg of powder and tamped flat, the tablet was centered in cavity, and an additional 200 mg of powder was added to cover the tablet, and compressed. The process was repeated with tablets each having 225 mg, 250 mg, and 275 mg in the bottom of the cavity, and the same amount covering the tablet.

Each tablet, including an uncoated one, was added to 40 mL of TSB in a beaker. A 300 µL sample of the buffer was removed at various times, and more samples were taken after the appearance of gas bubbles around the tablet, which is an indication that the tablet was near its bursting point. The absorbance of each buffer sample was measured at 550 nm on a SpectraMax 190 spectrometer (Molecular Devices, Sunnyvale, Calif.). The uncoated tablet dissolved completely within 5 minutes. Once the core dissolved completely, effervescent mixing created a homogenous solution. The bursting time for complete dissolution of the coated tablets was within 20-30 minutes from the appearance of a steady stream of gas bubbles from the tablet. This indicates a synergistic effect in releasing materials from a tablet between the disintegration aid in the core and gas bubbles produced by the effervescent material. FIG. 2 shows the quantitative bursting release profile of tablets with different amounts of coating in TSB by monitoring the absorbance at 550 nm. A tablet with about 225 mg or 250 mg of coating on each side could be useful for an enrichment media in which a 5.5-6.6 hour delay is desired for some organisms such as Listeria, while lower coating weights can be useful for enrichment media for organisms needing less time for growth.

Example 5. Coated Tablet with a Selective Agent and a 6 Hour Delayed Release

A core tablet composition was prepared using the composition in Table 3. Lithium carbonate was added to provide lithium ion to act as a selective agent for *Listeria Monocytogenes*. The materials were passed through a 30 mesh screen and then mixed and compressed into tablets according to the procedure described in Example 3. The composition was compressed in a tablet punch die with a 0.5 inch round cavity. The core tablet, weighing approximately 1 g, contained about 0.3 g of lithium carbonate. The hardness of the tablet was about 7 as determined by a tablet hardness tester (Dr. Schleuniger 8M; Pharmatron Inc.; Manchester N.H.)

A coating composition was prepared by manually vortexing the coating composition in Table 3 in a 200 mL glass jar for 2 minutes. The coated tablet was prepared according to the procedure described in Example 3 except that the tablet punch die had a 0.6875 diameter cavity and about 0.60 gram of the coating composition was placed in the bottom of the cavity and about 0.95 g of the composition covered the core tablet. A force of 5,000 pounds was used to compress the tablet. The tablet dissolved in about 6 hours in 40 mL of TSB.

TABLE 3

| | Compositions for Example 5 - weight % | |
|---|---|---|
| Material | Tablet | Coating |
| Silica Nanoparticles | 0.5 | |
| Magnesium stearate | 1.25 | 0.1 |
| HPC | 5 | 4.00 |
| Lithium carbonate | 30 | — |
| Citric acid | 52 | — |
| Sorbitol | 11.25 | — |
| ETC2 | 100 | 66 |
| HPMC | | 29.90 |

Example 6. Coated Tabled with Acriflavin and a 6 Hour Delayed Release

Core tablets were prepared using the tablet composition in Table 4 according to the procedure in Example 5. Each tablet weighed about 1 gram with about 0.6 milligram of acriflavin hydrochloride. The hardness of the tablets was about 7. The tablets were coated with the composition and procedure of Example 5 except that approximately 0.45 g of the coating composition was used for the bottom layer and about 0.70 g was used to cover the tablet. The coated tablet dissolved in about 6 hours in 40 mL TSB at room temperature.

TABLE 4

| Materials | Tablet composition - Ex 6 - weight % VII |
|---|---|
| Silica Nanoparticles | 0.5 |
| Magnesium stearate | 1.25 |
| HPC | 5 |
| Sodium bicarbonate powder | 31 |
| Sodium carbonate powder | 9 |
| Citric acid powder | 34.51 |
| Sorbitol | 18.683 |
| Acriflavin HCl | 0.06 |

Example 7. Coated Tablet with Acriflavin and Lithium and 6 Hour Delayed Release

Core tablets were prepared according to the procedure for Example 5 using the composition in Table 5 with two selective agents for *Listeria monocytogenes*, and two effervescent reagents (lithium carbonate and citric acid). Each tablet weighed about 1 gram with 0.26 g of lithium carbonate and 0.6 mg of acriflavin hydrochloride. The hardness of the tablets was about 7. An over-coating layer shown as Table 3 (coating) was applied the core tablet in a 0.6275 inch punch die made through Natoli Engineering (St Louis, Mo.). A coating powder of 0.38 gram for both top and bottom was applied as described in Example 5, and pressed at 3200 pounds. A tablet dissolved in about 6 hours in 40 mL of broth at 35° C.

TABLE 5

| Component | Tablet Composition (Example 7) wt % |
|---|---|
| SIL2 | 1 |
| Sodium Stearyl fumarate | 1.25 |
| Klucel EXF | 5 |
| Lithium carbonate | 26.2 |
| Citric acid | 45.41 |
| Sodium carbonate | 16.00 |
| Acriflavin chloride | 0.066 |
| Sorbitol | 4.82 |

Example 8. Detection of *Listeria monocytogenes*

A colony *L. monocytogenes* (ATCC 11994) from a streak plate culture is inoculated into Tryptic soy broth and incubated for 20-24 hours at 35° C. The overnight culture is diluted in Butterfield's Phosphate Diluent to provide a bacterial suspension with about 5000 cfu/mL (colony forming units/mL).

A 120 g portion of raw ground turkey, purchased from a local grocery store, is placed in a plastic bag and inoculated with about 0.4 mL of the bacterial suspension containing 2000 cfu of *L. monocytogenes*. The turkey is kneaded manually for about 5 minutes to mix the inoculum. The inoculated turkey is frozen at about −18° C. for about 36 hours and then allowed to thaw at 2-8° C. for 12 hours. A 20 g portion of turkey from the same package that is not inoculated but frozen and thawed, is used for a control.

A broth medium is prepared having a composition similar to a Fraser broth such as the composition shown in Table 6, without selective agents, i.e., lithium chloride and acriflavin HCl. The broth medium is steam sterilized.

A sample is prepared by adding 100 milliliters of the sterile broth medium and 10 g of thawed inoculated turkey to a stomacher bag with a filter (3M™ Homogenizer Bag—6469; 3M Company; St. Paul Minn.). The sample in the bag is homogenized for 30 seconds at 230 rpm on a stomacher (Stomacher 400 Circulator; Seward; West Sussex UK). Immediately before incubating, a tablet from Example 7 is added to the bag for Sample 1. Four other samples are prepared in the same manner with reagents added as follows: a tablet from Example 7 are added to each of 2 bags for Samples 2 and 3, which are duplicates of Sample 1; Sample 4 is prepared by adding liquid reagents (0.1 mL of a solution of 6 mg/mL of acriflavin HCl (prepared in reverse osmosis water) and 0.5 mL of a solution of 300 mg/mL of LiCl (prepared in reverse osmosis water) immediately to the bag (t=0). Sample 5 is prepared by adding the same amount of liquid reagents to the bag after 6 hours (t=6) of incubation. Sample 6 is prepared in the same way except that no actives are added. Sample 7 is a negative control sample prepared with the only the broth medium and turkey that was not inoculated.

All samples are placed into a 35° C. incubator. After 6 hours of incubation at 35° C., Sample 5 is removed from the incubator and the acriflavin and LiCl solutions are added. The samples are returned to the incubator and, after 18, 20, 22 and 24 hours, respectively, 5 mL samples of the filtrate are removed, placed into sterile polypropylene test tubes and frozen at −18° C. for subsequent sample preparation. The bags are returned to the incubator after each sample is removed.

The samples are prepared for PCR analysis using a sample preparation kit (PrepSEQ™ Spin Sample Preparation Kit, Product number N 4409735; Applied Biosystems; Foster City Calif.). Duplicate 600 microliter volumes of each collected sample are pipetted into microcentrifuge spin columns and the DNA is prepared according to the manufacturer's instructions. Samples are prepared in duplicate.

An overnight culture of *L. monocytogenes* (ATCC 11994- prepared as described above) is diluted sequentially by serial 10-fold in 10 millimolar phosphate buffer, resulting in suspensions of bacteria having from about $10^8$ to about $10^1$ cfu/mL (assuming the overnight culture has about $10^9$ cfu/mL). Diluted suspensions having about $10^2$ and $10^1$ cfu/mL, respectively, are plated on a culture device (e.g. a 3M™ Petrifilm™ Aerobic Count Plate; 3M Company; St Paul Minn.) for an accurate cfu determination. 600 µL-aliquots of the bacterial dilutions having about $10^6$ to about $10^2$ cfu/mL, respectively, are also processed for PCR analysis in a manner similar to the processing of the turkey samples, as described below.

The 600 µL samples are loaded to a prefilter column on a microcentrifuge tube and centrifuged at 14,000 rpm for 4 minutes, the top prefilter column is discarded, and the supernatant from each sample is aspirated and discarded. A 50 microliter volume of lysis buffer from the kit is added to the tube and then 10 microliters of Proteinase K solution (20 mg/mL Proteinase K solution, Molecular Biology Grade; Sigma Aldrich; St. Louis Mo.) is added. The samples are incubated at 55° C. for 30 minutes and then boiled at 100° C. for 10 minutes. After cooling to about room temperature 260 microliters of DNAase free water (Invitrogen; Carlsbad Calif.) is added to each microcentrifuge tube and centrifuged to 14,000 rpm for 1 minute. The clear supernatant from each spin column is used for Real-time PCR measurements.

Real-time PCR tests are performed using a TaqMan® *Listeria monocytogenes* Detection Kit (PN 4366102); Applied Biosystems; Foster City Calif. according to the manufacturer suggested protocol, i.e. 12 microliters from each boiled sample and 18 µL of PCR premix are pipetted into a 96-well PCR plate (MicroAmp plate; Applied Biosystems; Foster City Calif.). The PCR plate is sealed with a transparent tape and gently mixed by vortexing. Real-time PCR measurement is carried out on a Stratagene Mx3005P QPCR System (Agilent Technologies, Santa Clara, Calif.) with data analysis software (MxPro) to determine the Ct values.

Example 9. Controlled-Release Selective Reagents for Growing Heat-Stressed Cells A colony of *Listeria monocytogenes* (ATCC 19111) is obtained from an SBA streak plate and is inoculated into 5 mL of sterilized TSBYE (Trypticase Soy Broth with 6 g/L Yeast Extract, both obtained from Becton Dickinson and prepared according to manufacturer's instructions; Sparks Md.). The inoculated broth culture is incubated at 35° C. for 18 hours. A 4.5 ml volume of TSBYE in a Falcon tube is heated in a water bath maintained at 55° C. for 30 minutes.

A 0.5 mL volume of the broth culture is added to the tube and vigorously vortexed for 3-5 seconds. A stressed cell culture is prepared by incubating the diluted culture in the 55° C. water bath for precisely 10 minutes and then immediately placed in an ice bath for 30 minutes.

A similarly treated dilution of the broth culture that is not heat treated is also placed in the ice bath. Both cultures are serially diluted (10-fold dilutions; 0.1 mL into 0.9 mL of Butterfields Phosphate diluent), and 0.1 mL of the dilution is plated onto a MOx agar plate and also onto a SBA plate and duplicates of each are also plated. The plates are incubated at 35° C. for 48 hours and are then enumerated to determine the colony count and the % stressed cells.

A broth medium is prepared having a composition similar to a Fraser broth such as the composition shown in Table 6, without selective agents, i.e., lithium chloride and Acriflavin HCl. The broth medium is steam sterilized.

TABLE 6

| Material | Final Concentration - (g/L) |
|---|---|
| Pancreatic Digest of Casein | 5 |
| Proteose Peptone No. 3 | 5 |
| Beef Extract | 5 |
| Yeast Extract | 5 |
| Sodium Chloride | 20 |
| Disodium Phosphate | 9.6 |
| Monopotassium Phosphate | 1.35 |
| Esculin | 1.0 |
| Nalidixic acid, sodium salt | 0.02 |

Heat-stressed cell cultures are prepared and subjected to two serial 10-fold dilutions in Butterfield's Phosphate Diluent, and 0.05 ml of the last serial dilution is added to 100 mL of the broth medium in a stomacher filter bag (Homogenizer bag, part number 6469; 3M Company, St Paul, Minn.). The final concentration in each bag is about 20 cfu/mL of broth medium. The bags are sealed and processed for 30 seconds at a setting of 230 rpm on a stomacher (Stomacher 400 Circulator; Seward; West Sussex UK).

The selective agents shown in Table 7 are added to each of the respective the stomacher bags immediately before incubating at 35° C. (t=0), or after 6 hours of incubation (t=6). During incubation, 5 mL samples are removed from each bag after 19 hours, 21 hours and 24 hours. Bags are returned to the incubator after each sample is taken.

Viable cells from each sample are enumerated on MOx agar plates as follows: 5 milliliter aliquots are subjected to six serial 10-fold dilutions in Butterfields Phosphate Diluent and then duplicate 0.1 mL portions of each dilution are spread onto MOx agar plates and incubated at 35° C. for 48 hours. The colonies on each plate are counted and are reported as an average log cfu for each set of duplicate plates.

TABLE 7

| Bag | Reagents Added |
|---|---|
| 1 | None |
| 2 | *Li/ACF liquid added immediately |
| 3 | *Li/ACF liquid added after 6 hours of incubation |
| 4 | **Coated tablet 1 added immediately |
| 5 | **Coated tablet 2 added immediately |
| 6 | **Coated tablet 3 added immediately |

*Li/ACF - 0.1 mL of 6 μg/mL acriflavin and 0.5 mL of 600 mg/mL of LiCl
**Coated tablets that are prepared according to Example 7.

Examples 10-12 Pouches for Controlled Release of Active Agents

Polyvinyl alcohol films having the grade and thickness for examples 10-12 as shown in Table 8 were obtained under the SOLUBLON trade name from Aicello Chemical Co.; Toyohashi, Japan. Pieces measuring about 2 inches (5 cm) by about 3 inches (7.5 cm) are cut and heat sealed on 3 sides to form a pouch. A mixture of sodium bicarbonate and citric acid in a 1:1 ratio with about 0.1% phenol red was prepared and about 2 grams were added to each of the pouches, and the last side was heated sealed.

Each of the pouches was immersed in 200 mL of water at room temperature and the time for bursting of the pouch was recorded and is shown in Table 8. Just before bursting, the bubbles were generated around the pouch where it had started to dissolve. Within a few seconds, the pouch burst and the effervescent material rapidly mixed the dye in the water.

TABLE 8

| Example | Film Grade | Film Thickness | Solubility | Time to burst |
|---|---|---|---|---|
| 10 | EF-30 | 30 microns | Hot water | About 5 minutes |
| 11 | BP-26 | 26 microns | Warm water | About 1 minute |
| 12 | KA-40 | 40 microns | Cold water | About 30 seconds |

Examples 13-14 Capsules for Controlled Release of Active Agents

A homogenous powder was prepared by mixing 100 g of a 2:1 mixture sodium carbonate and citric acid with 0.1% phenol red, and grinding this mixture with 20 g of sorbitol. Size 4 HPMC capsules were filled manually with the mixture and each capsule weighed approximately 215 mg. The closed capsule was then manually dip-coated into an ethanolic solution of 10% Eudragit S100 polymer and 5% triethyl citrate for Example 13. For Example 14, a second layer was overcoated onto the first layer. The capsules were each placed in 15 mL of PBS buffer. A capsule without coating dissolved within minutes. The single coating delayed the release time to 1.5 hour and the two-layer coating delayed release to about 3.5 hour delay of the release time.

Example 15. Growth of Bacteria Using a Selective Agent Delivered in a Tablet

Tablets were prepared according to the procedure of Example 3 using the compositions shown in Table 9. The tablets nominally weighed 100 milligrams/tablet (mg/tablet) and each had a diameter of 0.2817 inch (0.716 cm) with a convex shape. The tablets were pressed at 1000 pounds.

TABLE 9

| Component | Tablet 1 Mg/100 mg tablet | Tablet 2 Mg/100 mg tablet |
|---|---|---|
| Sil2 | 1.0 | 1.00 |
| Lutrol ® micro 127* | 6.0 | 6.00 |
| HPC | 5.0 | 5.00 |
| Sodium carbonate | 35.0 | 0 |
| Sodium bicarbonate | 0 | 35.00 |

TABLE 9-continued

| Component | Tablet 1 Mg/100 mg tablet | Tablet 2 Mg/100 mg tablet |
| --- | --- | --- |
| Citric acid | 28.0 | 26.68 |
| Ceftazidime hydrate | 10 | 10.00 |
| Sorbitol | 14.81 | 16.32 |
| Total | 100.00 | 100.00 |

*LUTROL micro 127 - Methyl-oxirane polymer with oxirane; BASF Corporation; Florham Park, NJ Samples of growth media were prepared by dissolving a tablet of each composition in 1 liter of recovery media (modified *Listeria* Recovery Broth (MLRB), available from 3M Company; St. Paul, Minn.). The tablets dissolved within 4.5 minutes. A sample of growth media was prepared as a control by dissolving 10 mg of Ceftazidime hydrate powder (product number C3809-5G available from Sigma Aldrich; St. Louis, Mo.) in 1 liter of MLRB. Six dilutions of growth media were prepared to obtain concentrations of Ceftazidime hydrate (CDH) shown in Table 9.

A bacterial suspension was prepared by inoculating a pure culture of *Pseudomonas putida* (ATCC 31483 obtained from ATCC, Manassas, Va.) into tryptic soy broth (BD™ Tryptic Soy Broth; Becton Dickinson; Sparks, Md.) and incubating at 37° C. The suspension was diluted 1:1,000 in SMB (Standard Methods Buffer; 3M Company; St. Paul, Minn.). The diluted suspension was further diluted 1:10,000-diluted in SMB growth medium containing ceftazidime concentrations shown in Table 10. Four duplicates of each sample were pipetted into a 96-well plate as follows: Growth Control with no Ceftazidime hydrate; an Undiluted Control with 10 micrograms Ceftazidime hydrate/microliter of the bacterial suspension; and each dilution of inoculated medium containing the concentration of ceftazidime hydrate shown in the Table 10. The 96-well plate was incubated overnight at 37° C. and examined visually for bacterial growth. Turbidity in the well indicated growth.

TABLE 10

| Sample | Tablet 1 | Tablet 2 | Powder Control |
| --- | --- | --- | --- |
| Growth Control - No antibiotic | + | + | + |
| Undiluted Control - 10 mcg CDH/microliter* | − | − | − |
| 8.75 mcg CDH/microliter | − | − | − |
| 7.5 mcg CDH/microliter | − | − | − |
| 6.25 mcg CDH/microliter | − | − | − |
| 5.0 mcg CDH/microliter | − | − | − |
| 3.75 mcg CDH/microliter | + | + | + |
| 2.5 mcg CDH/microliter | + | + | + |

*mcg CDH/microliter = micrograms of Ceftazidime hydrate per microliter of sample
"+" indicates growth;
"−" indicates no growth The data in Table 10 show that the delivery of a selective agent in a tablet was comparable to delivering the selective agent in a powder and the lowest concentration of ceftazidime hydrate showing no growth was 5 mcg/microliter of sample.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of enriching the growth of a target microorganism, comprising:

providing a culture medium, a sample that includes the target microorganism, and a latent effervescent body;

wherein the latent effervescent body comprises an outer shell with a core composition disposed therein;

wherein the core composition comprises two or more effervescent components and a selective agent that facilitates the growth of the target microorganism relative to growth of at least one microorganism other than the target microorganism;

contacting the sample, the latent effervescent body, and the culture medium under aqueous conditions to facilitate growth of the target microorganism;

allowing the target microorganism to grow over a time period of about 2 hours to about 6 hours; and releasing the selective agent from the latent effervescent body after a time period of about 2 hours to about 6 hours;

wherein releasing the selective agent further comprises distributing the selective agent in the culture medium;

wherein distributing the selective agent comprises distributing the selective agent via a mixing process resulting from gaseous effervescence;

wherein releasing the selective agent comprises delaying the release of the selective agent for a predetermined time after the step of contacting the sample, the latent effervescent body, and the culture medium under aqueous conditions.

2. The method of claim 1, wherein contacting the sample, the latent effervescent body, and the culture medium further comprises contacting the sample with an effective amount of released selective agent for a period of time sufficient to permit selective enrichment of the target microorganism.

3. The method of claim 1, further comprising detecting a microorganism.

4. The method of claim 3, wherein detecting the microorganism comprises propagating the microorganism on or in a semisolid culture medium, observing the microorganism microscopically, detecting metabolic activity of the microorganism, detecting a biomolecule of the microorganism, or detecting a nucleic acid of the microorganism.

* * * * *